United States Patent [19]

Graf

[11] 4,109,145
[45] Aug. 22, 1978

[54] APPARATUS BEING CONTROLLED BY MOVEMENT OF THE EYE

[75] Inventor: Carl P. Graf, Forrest Lake, Minn.

[73] Assignee: Honeywell Inc., Minneapolis, Minn.

[21] Appl. No.: 471,409

[22] Filed: May 20, 1974

[51] Int. Cl.² .............................................. G01J 1/20
[52] U.S. Cl. ................................. 250/201; 250/221; 250/203 R; 340/152 R
[58] Field of Search ............... 250/203, 201, 271, 216, 250/221; 351/6, 7; 33/227, 228

[56] References Cited

U.S. PATENT DOCUMENTS

| | | | |
|---|---|---|---|
| 3,136,839 | 6/1964 | Safir | 351/6 X |
| 3,375,375 | 3/1968 | Abbey et al. | 250/216 |
| 3,379,885 | 4/1968 | Nork | 250/338 |
| 3,478,220 | 11/1969 | Milroy | 250/221 |
| 3,507,988 | 4/1970 | Holmes | 250/221 X |
| 3,620,601 | 11/1971 | Waghorn et al. | 250/221 X |
| 3,698,811 | 10/1972 | Weil | 356/28 |
| 3,718,386 | 2/1973 | Lynn et al. | 351/23 |
| 3,746,432 | 7/1973 | Mason | 250/201 X |
| 3,806,725 | 4/1974 | Leitz | 250/221 X |
| 3,864,030 | 2/1975 | Cornsweet | 351/7 |

OTHER PUBLICATIONS

Stein: Aviation Week & Space Technology, 1/28/74, pp. 52-55.
Merchant et al: A Remote Oculometer Permitting Head Movement (AMRL-TR-73-69), Nov. 1973, pp. I-V; 1-29.

*Primary Examiner*—Alfred E. Smith
*Assistant Examiner*—David K. Moore
*Attorney, Agent, or Firm*—Charles J. Ungemach

[57] ABSTRACT

Line of sight detecting apparatus such as an oculometer produces signals indicative of the direction along which an operator is looking. A display with predetermined positions thereon is positioned for viewing by the operator. A computer receives the signals from the line of sight detecting apparatus and utilizing a timing function determines when the operator's line of sight is directed toward one of the predetermined positions on the display for a predetermined length of time. Depending upon which of the predetermined positions is viewed by the operator for the predetermined time period, the computer produces a signal which is used to produce various images, such as indicator readings, or to produce various control functions for the operator.

8 Claims, 3 Drawing Figures

APPARATUS BEING CONTROLLED BY MOVEMENT OF THE EYE

BACKGROUND OF THE INVENTION

This invention relates to apparatus for using the human eye to produce outputs for switching or otherwise controlling machinery and more particularly apparatus for monitoring eye orientation and, upon detecting a predetermined orientation of duration longer than a predetermined time, for producing a signal usable for control of machinery. There are a number of situations where a human being wishes to control certain equipment while at the same time keeping his field of vision within a certain range. Often these situations involve the use of the operator's hands to an extent where additional control requirements for the hands are undesirable. For example, an aircraft pilot under circumstances such as landing desires to keep his eyes trained on the outside world through his windshield. During the landing procedure his hands and feet are also busy with manipulation of the aircraft into the desired landing path. During such times the pilot may also desire to know the indications which appear on one or more of his instruments but it may be risky for him to remove his concentration from the outside scene and glance toward these instruments even for a few seconds. He may also desire to manipulate several switches during the procedure again requiring him to remove his concentration from the outside scene and locate the proper switches for manipulation by his already busy hands.

The present invention is intended to simplify some of the manipulations required by the human operator of an aircraft or other machine and to allow the operator to accomplish some of the manipulations by using eye movements without changing his desired field of view.

DESCRIPTION OF THE PRIOR ART

Apparatus for detecting the orientation of an eye or determining its line of sight is known in the art. Occulometers such as are found in U.S. Pat. Nos. 3,749,432 issued July 17, 1973 and 3,462,604 issued Aug. 19, 1969 perform this function as do Eye Trackers such as are found in U.S. Pat. Nos. 3,712,716 issued Jan. 23, 1973 and 3,724,932 issued Apr. 3, 1973. Helmet mounted line of sight determining apparatus such as is found in U.S. Pat. No. 3,375,375 issued Mar. 29, 1968 are also capable of producing signals indicative of the orientation of the eye of a machine operator such as an aircraft pilot. Such apparatus has been found capable of detecting the direction that an eye is looking to within remarkably small increments in the order of one-half of a degree and less.

Apparatus for projecting images into the field of view of an operator and showing, for example, instrument readings is also known in the art. Head up displays, such as found in U.S. Pat. Nos. 3,697,154 issued Oct. 10, 1972, and 3,737,212 issued June 5, 1973, and viewing devices such as shown in U.S. Pat. Nos. 3,446,919 issued May 27, 1969, and 3,711,826 issued Jan. 16, 1973, all show systems for allowing a machine operator, such as an aircraft pilot, to view instrument readings and the like without having to remove his vision from the outside scene by superimposing the images into his line of sight.

It has also been suggested in the prior art that certain control functions could be generated using movement of the eye. For example, in the above mentioned U.S. Pat. No. 3,375,375, the described apparatus is suggested for use with an aircraft weapon system to aim or guide the weapons toward a desired target in accordance with the direction of the pilot's line of sight.

All of the prior art apparatus suffers from one or more disadvantages which the present invention overcomes. In the head up display apparatus, although an image of one or more instrument readings can be combined into the field of view of the operator, in order to change from one instrument reading to another, the operator must glance away from the field in order to identify the proper switch or button to actuate and must manipulate the switch manually. In the case of aircraft, this not only introduces the danger that the pilot will miss some important event occurring outside of the aircraft but also that his hands or feet will have to be utilized momentarily for an action other than controlling the aircraft. The present invention permits these operations to be performed by the eye while trained in the desired field of view.

In the art suggesting control of other instruments such as aircraft weapons by line of sight determining apparatus, the proposed control is automatic and continuous. The operation is performed with or without the operator's volition unless manually overridden or controlled. Furthermore, since the human eye tends to more or less continuously wander throughout the field of view, the apparatus being controlled will do much useless wandering also. Finally, the prior art does not provide the operator with feedback to inform him that the control functions he commands are being performed. The present invention permits the operator to choose what to control and when to control it with intentional eye movements and without the necessity of manual intervention and provides indications which assure the operator that his commands have been executed.

BRIEF SUMMARY OF THE INVENTION

The present invention utilizes an occulometer or other line of sight determining device to monitor the orientation of the eye. Apparatus is provided, however, which keeps the signals produced by the occulometer from producing any control function until the operator willfully directs it. This is accomplished by requiring the operator to direct his line of sight in a predetermined direction for a predetermined length of time before the equipment will produce a control output. The predetermined length of time may be set small enough to only avoid the continual wandering problem mentioned above or large enough that it is substantially assured that such line of sight has not been accidentally assumed. Alternately, the apparatus may be set to respond only after the operator has set his line of sight in a first direction for a first time period and then in a second or even third and fourth directions for additional time periods. Thus, by monitoring not only the direction of the line of sight but also the time period it is maintained before permitting a control signal to occur, unnecessary and accidental outputs can be avoided.

Various other objects, advantages and features of novelty which characterize the present invention are pointed out with particularity in the claims annexed hereto and forming a part hereof. For a better understanding of the invention, its advantages and uses, reference should be had to the drawings which form a further part hereof, and to the accompanying descriptive matter, in which there is illustrated and described the preferred embodiments of the invention.

DESCRIPTION OF THE PREFERRED EMBODIMENTS

Figure 1:
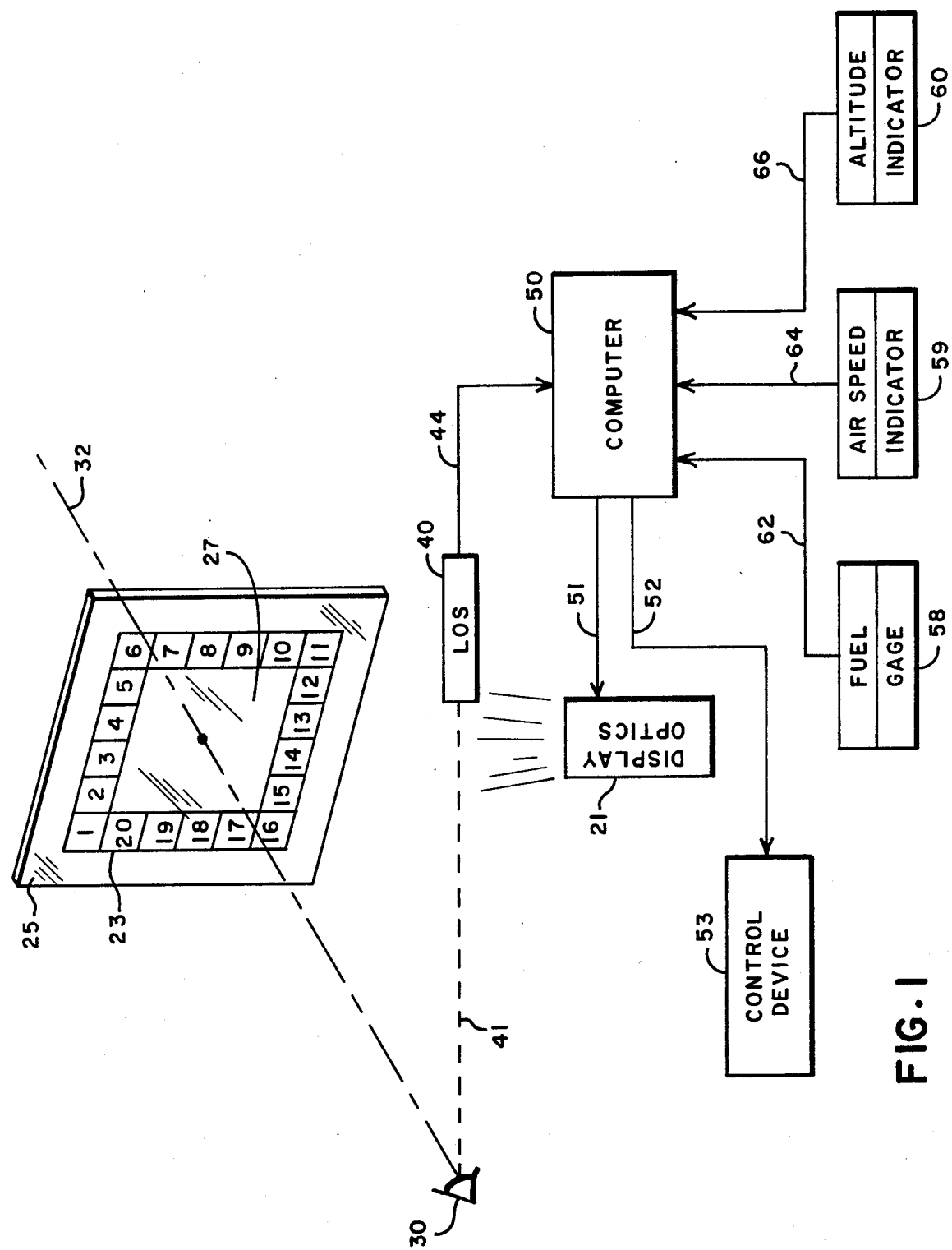
FIG. 1 is a plan view of a preferred embodiment of the present invention.

Referring to FIG. 1, a device shown as Display Optics 21 is shown projecting a display 23 onto a screen 25. Display Optics 21 may be a standard slide projector, a cathode ray tube and optical system such as is shown in the above-mentioned U.S. Pat. Nos. 3,697,154 and 3,737,212, or any other device capable of receiving an input signal and operable in accordance therewith to produce various images to an observer for viewing. When the invention is to be used for aiding an aircraft pilot, screen 25 may be, for example, the windshield of the aircraft, a partly silvered glass or the face shield of a helmet visor.

The projected display 23 will be explained in greater detail in connection with FIG. 2 and is shown in FIG. 1 as a series of squares or trigger areas numbered 1 through 20 and arranged in rectangular fashion around a central area 27. As will be explained, the central area 27 is used to receive projected images for viewing by the observer while the display 23 is used by the observer to select a desired control function or to determine which of a plurality of available displays, such as instrument readings, is to be projected into the central area 27. An observer's eye 30 is shown positioned so as to look at display 23 and through screen 25 to the scene beyond. A broken line 32 is drawn in FIG. 1 from the observer's eye through the center of the image 23 for reference purposes.

A line of sight determining device identified as LOS 40 in FIG. 1 is shown directed at the observer's eye 30 along a dashed line 41. The LOS 40 may be an occulometer, such as found in the above-mentioned U.S. Pat. Nos. 3,746,432 and 3,462,604, the above-mentioned helmet mounted apparatus of U.S. Pat. No. 3,375,375, or any other apparatus capable of producing an output indicative of the direction in which an eye is looking. In the preferred embodiment, a Model Mark 3 occulometer manufactured by Honeywell Inc. is used.

In FIG. 1, LOS 40 is shown having an output line 44 connected to an input of a computer 50. The signal on output line 44 is indicative of the line of sight direction of eye 30 form some arbitrary reference line, such as 32. Output line 44 may comprise two wires, one of which carries a D.C. signal of magnitude that varies with movements of eye 30 in a horizontal direction away from the reference line 32, and the other of which carries a D.C. signal of magnitude that varies with movements of eye 30 in a vertical direction away from the reference line 32. For example, if the oculometer of the above mentioned U.S. Pat. No. 3,746,432 were used, line 44 would comprise lines 51 and 60 found therein. The output on line 44 may also be two alternating signals or an alternating signal having two separately distinguishable components such as components in phase quadrature. In any event, the computer 50 will receive a signal which contains information of the horizontal and vertical movements of the eye and from which the instantaneous line of sight of eye 30 may be determined.

Computer 50, which in the preferred embodiment is a Nova 1220 mini computer manufactured by the Data General Corporation has an input which receives the signal on output line 44 and, if necessary, converts the signal to a form usable by the computer. With a D.C. signal on output line 44 and A/D converter supplied with the Nova 1220 is used. Computer 50 operates to produce a signal on an output line 51 to control the display optics 21 or to produce a signal on an output line 52 to produce a control function for a control device 53. Again, if necessary, an appropriate converter such as a D/A converter may be used to change the signal from the computer to a form usable by display optics 21 or control device 53. It would, however, be undesirable to have a continuously varying signal on output lines 51 or 52 accompanying every movement of the eye 30. Such a situation would result in a confusing number of images being projected onto screen 25 and accidental control functions being performed with possibly disastrous results.

According to the present invention, this problem is overcome by providing a timing function in the computer 50, or elsewhere in the circuit between the LOS 40 and the display optics 21 and control device 53. The Nova 1220 provides a clock option card which may be used. The timing function operates to prevent signals to the display optics 21 or the control device 53 unless the eye 30 has maintained a line of sight for a predetermined time period. For example, it has been found that some human eyes may "fixate", that is, direct and focus on a point or object, as often as seven times a second. Clearly then, signals which are maintained for time periods of less than that required for "fixation" would show that the sight of the operator had not intentionally focused on a point or object. In some people, or under different conditions, fixations may be capable of occurring only four times a second. Signals which are maintained for periods in excess of the time necessary for "fixation" to occur would tend to show that the operator had consciously focused on an object. To minimize accidental operations, the timing function should not allow signals to be presented to the switching circuit unless the operator's line of sight has been maintained at least as long as it takes the operator to "fixate". On the other hand, the length of time for maintaining a fixed line of sight prior to instituting a signal to display optics 21 or control device 53 may be considerably longer so as to further assure that unwanted signals do not occur. In the preferred embodiment, the timing is preferably in the order of three tenths to one half second.

The desired fixation is determined using the clock option card of the Nova 1220 by sampling the output of the LOS 40 at 20 millesecond intervals although other sampling intervals may be used. When the timing is set at ½ second, the average value of the output of LOS 40 for 25 consecutive samples is taken and this average is compared with each of the individual samples. This procedure is used because it has been discovered that even when the eye is fixating on a point or object, there is a slight tremor in the eye which will produce minor variations in the output of the LOS 40. There is also a small variation in output due to noise in the electronics involved. Accordingly, even with fixation, small variations in voltage, in the order of perhaps 10 to 30 millivolts occur. The magnitude of these variations may be predetermined and programmed into the computer.

Then to determine that fixation has occurred, computer 50 examines the differences between the average of the samples and the value of each sample and if none of these differences exceed the predetermined amount, say 40 millivolts, fixation is deemed to have occurred. If the timing was to be set at three tenths of a second then fifteen consecutive twenty millisecond samples would be taken and if the differences between the average value and each of the fifteen samples does not exceed the predetermined amount, "fixation" would be deemed to have occurred. After each sample is obtained, it is added into the computer storage and the oldest previous sample in storage is discarded. In this way, continuous updating of the samples and their average is obtained.

The amount of variation from an absolutely fixed line of sight which will be allowed may differ for different situations. In the present case where the individual squares in display 23 occupy one sixth of the horizontal and vertical distances of the whole display, variations from the center of a square as high as one sixth of the total horizontal and vertical variation might be permitted. Generally speaking, however, the amount of permissible variation should be set considerably lower to assure that the operator really is intentionally looking at one of the squares. This will be explained in greater detail in connection with FIG. 2. Properly programming the computer 50 sets the two conditions, i.e., the amount of variation from an absolutely fixed line of sight which will be allowed and the time necessary for that line of sight to be maintained before a "fixation" is deemed to have occurred. Computer 50 will produce no signals on output lines 51 or 52 until these programmed conditions have been satisfied.

In addition to timing the duration of the signals from LOS 40 to establish when "fixation" has occurred, computer 50 uses the components of the signal on output line 44 to determine the direction eye 30 is sighting to establish which, if any, of the squares in display 23 the operator is looking at. This is accomplished by analyzing the magnitude of the components of the signal on output line 44 to determine the ordinate and abscissa of the intersection of the operator's line of sight with the plane of display 23. The limits of each of the squares in terms of signals indicative of their horizontal and vertical position is predetermined and stored in the computer 50. The signals from LOS 40 are then compared with the stored signals in the computer 50 memory and if the signals from LOS 40 fall within the limits established for a given square, the operator is deemed to be directing his gaze at that square.

When a fixation on a selected one of the squares in display 23 is determined to have occurred, computer 50 will produce an output on output line 51 or 52 depending on the desired display or control function represented by the selected square.

More particularly, when computer 50 determines that "fixation" has occurred, then the signal on output line 44 is analyzed by computer 50 to determine which, if any, of the numbered squares on display 23, eye 30 is directed toward as explained above. Depending upon which of the numbered squares in display 23 is determined to be in the observer's line of sight, a signal being presented to computer 50 from one of a plurality of subsystems indicated in FIG. 1 as fuel gage 58, airspeed indicator 59 or altitude indicator 60 via output lines 62, 64 and 66, respectively, is switched into the computer. Subsystems 58, 59 and 60 may be the standard gages and indicators utilized in the aircraft. The signals supplied by subsystems on output lines 62, 64 and 66, each indicative of the quantity being indicated by the subsystem, may be scaled and converted, such as by an A/D converter for use by computer 50. Depending on the magnitude of the signals, computer 50 will operate to produce the appropriate signal to be used in controlling display optics 21 or control device 53. When the desired indication appears on screen 25, it provides the feedback to the operator showing that the desired command has been executed.

Of course, while three subsystems have been shown in FIG. 1, there will be as many subsystems as there are desired displays. Likewise, while one control device 53 has been shown, there may be as many control devices as desired.

Figure 2:
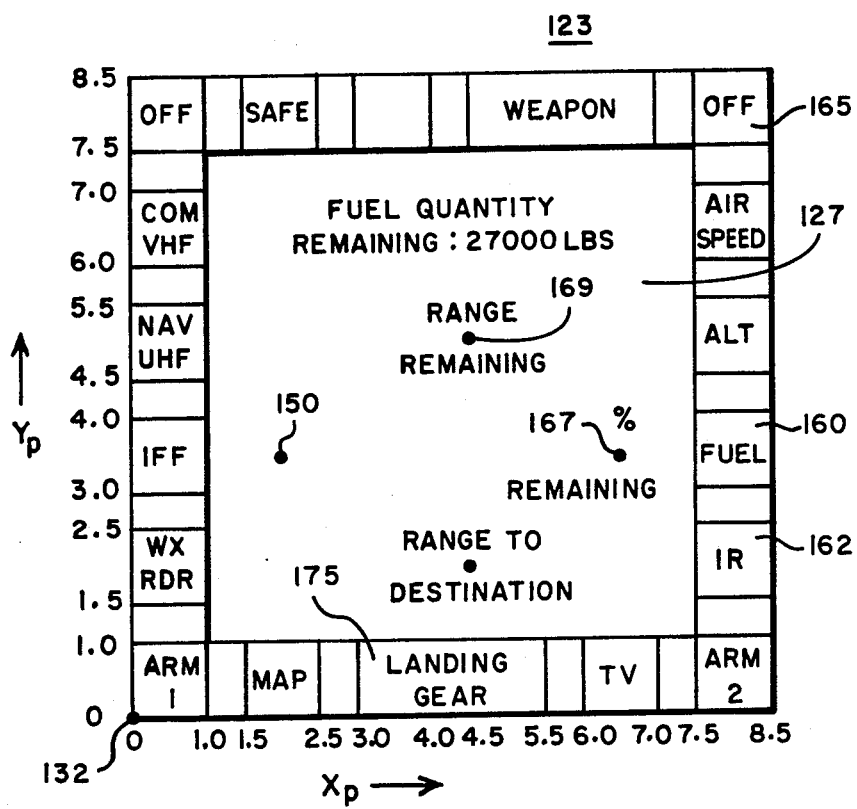
FIG. 2 is a detail drawing showing an example of an image which may be formed in the field of view of the eye of FIG. 1.

Referring now to FIG. 2, there is shown a more detailed example of a display 123 such as was shown in FIG. 1 as display 23.

Display 123 is shown as having various trigger areas as shown as squares and rectangles arranged in a square pattern around a central area 127. In this example, the reference axis 132 is set to be in the lower left hand corner although its position is arbitrary. As established, when the operator's line of sight is directed at the lower left hand corner where axis 132 intersects the plane of display 123 and the abscissa and ordinate of the coordinate system are zero, the output of the LOS 40 of FIG. 1 will be zero or some fixed reference voltage for both the horizontal and vertical directions. In FIG. 2 the horizontal direction is shown extending to the right from reference axis 132 in the direction identified as $X_p$ and the vertical direction extending upward from axis 132 in the direction $Y_p$.

As the operator's line of sight moves in the direction $X_p$, the voltage from LOS 40 of FIG. 1 indicative of horizontal movement of the eye 30 will change while the voltage indicative of vertical eye movement will remain fixed. As the operator's line of sight moves in the $Y_p$ direction, the voltage from LOS 40 to FIG. 1 indicative of vertical movement of the eye 30 will change while the voltage indicative of horizontal movement will remain fixed.

As the operator's line of sight moves around within the area defined by the display 123, the voltage from LOS 40 of FIG. 1 will have components indicative of both vertical and horizontal movement of the eye 30. At any position within the area, there is a definite voltage output from the LOS 40 of FIG. 1 which establishes the ordinate and abscissa of the intersection of the operator's line of sight with the surface of display 123.

Along the lower horizontal and left side vertical edges of the display 123 in FIG. 2, there are numbers shown from 0 to 8.5 representing voltages which might occur from LOS 40 as the eye 30 of FIG. 1 moves in the $X_p$ and $Y_p$ directions. Again, these voltages are arbitrary and depend upon the kind of line of sight determining device used and the reference voltage chosen.

In FIG. 2 if the eye 30 of FIG. 1 were to fixate on a point identified by reference numeral 150, the LOS 40 of FIG. 1 would produce an output of approximately 2.0 volts for the $X_p$ component and an output of approximately 3.5 volts for the $Y_p$ component. If the LOS 40 output contained 8.0 volts for the $X_p$ component and 3.5 volts for the $Y_p$ component, the eye would be directed approximately at the center of square 160 upon which the word "FUEL" is shown. It is thus seen that the horizontal and vertical components of the output from LOS 40 in FIG. 1 can be used to establish the point where the operator's eye is directed.

In FIG. 2 the individual squares and rectangles of display 123 are separated from each other by a small space which has been exaggerated in size for clarity. For example, the square 160 upon which the word "FUEL" has been shown occupies a space extending in the $X_p$ direction from 7.5 to 8.5 volts and in the $Y_p$ direction from 3 to 4 volts. The next square 162 downward from square 160 upon which "IR" has been shown occupies a space extending from 7.5 to 8.5 volts in the $X_p$ direction and from 1.5 to 2.5 volts in the $Y_p$ direction. The band between squares 160 and 162 occupies a space extending from 7.5 to 8.5 volts in the $X_p$ direction and from 2.5 to 3.0 volts in the $Y_p$ direction. These bands between the squares operate to prevent overlapping indications at the border lines, that is, should the squares be directly touching one another, then when the operator's eye is directed at the joining line between the two, the output of LOS 40 would not be able to establish upon which of the squares the operator was intending to fixate. Of course, the band areas may be programmed into the computer which would then automatically reject any signal falling within the limits set.

Referring again to FIG. 2, assume for the moment that the central area 127 was blank and that the operator, who in this case is considered to be an aircraft pilot, wishes to know what his aircraft fuel quantity situation is. He would direct his line of sight to focus on the square 160 which bears the indication "FUEL". A signal from LOS 40 in FIG. 1 having an $X_p$ component between 7.5 volts and 8.5 volts and a $Y_p$ component between 3.0 volts and 4.0 volts would be presented to computer 50 via output 44. As explained above, computer 50 would compare these signals with those stored in its memory and determine that the operator's line of sight was directed so as to require a fuel quantity display in the area 127. The computer would also determine, by the procedure explained earlier, that "fixation" had occurred or that the line of sight had not changed for the predetermined time period. Computer 50 would then utilize the signal from fuel gage subsystem 58 of FIG. 1 and would, upon receipt of the desired information, produce a signal in a form acceptable to display optics 21 on output 51 indicative of the desired display. Display optics 21 would then produce an image in the central area 127 which might appear as shown in FIG. 2. Once the image appears in the central area 127 showing that the desired command had been executed, it will remain until the operator desires to remove it, by, for example, fixating on a square 165 in the upper right hand corner of display 123 and labeled "OFF". The display could also be programmed to remain for a predetermined period and then automatically shut off.

The operator may observe the image of the fuel quantity remaining and decide that he would like to know the percent of fuel remaining.

In this case, he would fixate on the point 167 labeled "% REMAINING". At this time the LOS 40 would produce a signal having an $X_p$ component of 6.5 volts and a $Y_p$ component of 3.5 volts. Computer 50 would determine this new line of sight by comparing these signals with preprogrammed signals and after also determining that "fixation" had occurred would present a signal to the display optics which would change the image in the central area 127 to indicate the percent of full tanks remaining. This information could, for example, appear below the already existing indication of fuel quantity. Similarly, the operator might wish to know the range his aircraft has with this amount of fuel, in which case he need only "fixate" on point 169 in FIG. 2 and the desired information would appear assuming the computer receives other information, such as airspeed, wind velocity and direction from apparatus (not shown) and is programmed to calculate range.

As mentioned earlier, it is also possible to perform control functions with the present invention. For example, should the pilot desire to utilize the present invention to accomplish a lowering of his landing gear during landing procedure, he would fixate on square 175. Since this operation could be dangerous if accidentally performed, it would be preferable not to have a fixation or square 175 automatically lower the landing gear. Rather, a new display might appear in area 127 which had several identified points imaged therein and in order to actually produce a signal from computer 50 to the control device 53 which will be assumed in this case as operable to lower the landing gear, the operator must first fixate on these additional points in a predetermined order. Thus, for computer 50 to produce the desired signal on output 52, the computer would have to first determine a fixation on square 175 and then several follow-on fixations. Such a procedure would minimize the chance of accidental landing gear lowering. When the landing gear has been lowered, a signal may be presented to the display optics 21 so that an indication may be presented on screen 25 showing the operator that the desired command has now been executed.

Figure 3:
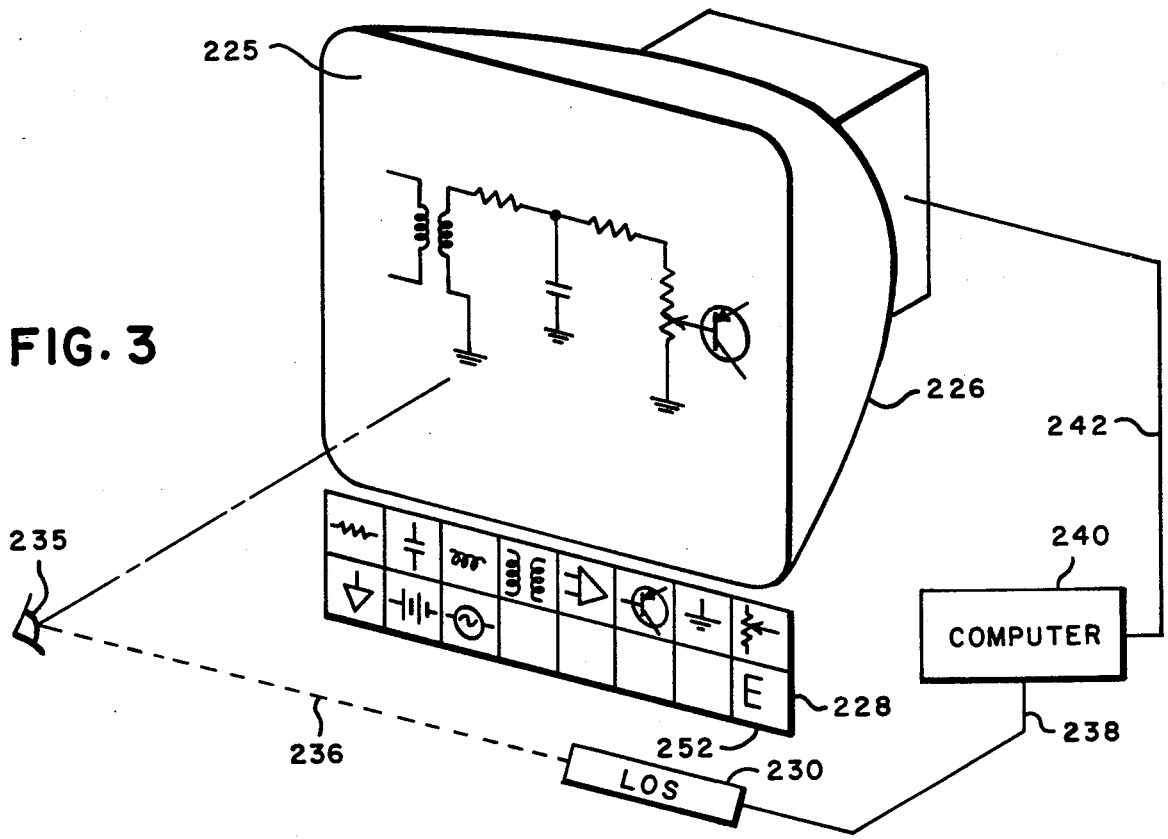
FIG. 3 is a plan view of an alternate embodiment of the present invention.

FIG. 3 shows an alternate embodiment of the present invention as an aid in circuit design. In this embodiment the operator observes a screen which, as shown, may be the face 225 of a CRT 226 or which may be a screen receiving a projection thereof through an optical system. The CRT is operable upon receipt of the proper input signals to produce and retain on its face representations of elements of circuits such as resistors, capacitors and the like.

Below the CRT, or at any convenient location, a display 228 containing a number of areas each of which depicts a circuit element is placed, a few of which have been shown in FIG. 3.

An LOS 230 which may be like the LOS 40 of FIG. 1 is shown being directed toward the operator's eye 235 by a dashed line 236. LOS 230 is shown having an output line 238 which may produce a signal like that heretofore described containing two components, one indicative of horizontal eye movement, and the other indicative of vertical eye movement. Output 238 is connected to a computer 240 which also may be of the type used in connection with FIG. 1. Computer 240 is connected to CRT 226 by a cable 242 so that computer 240 may control the operation of CRT 226 in accordance with the operator's desires.

In operation, computer 240, utilizing a process like that employed in connection with FIGS. 1 and 2, determines when eye 235 has fixated on one of the symbols on display 228. It then sends a signal to CRT 226 via cable 242 to generate the chosen symbol on the face 225. Thereafter, the LOS 230 follows the movement of eye 235 and computer 240 directs CRT 226 to move the chosen symbol across the face 225 following the line of sight of the operator. Accordingly, the operator need merely move his line of sight to the area on face 225 where he wishes to place the symbol and the symbol will move accordingly. After the symbol has been moved to the proper location on face 225, the operator will wish to fix the symbol so that it no longer follows his eye movements. In the preferred embodiment, this is accomplished by using the timing function of computer 240 and requiring the operator to maintain his line of sight at the desired location for a predetermined time period preferably longer than that used to determine fixation. For example, computer 240 may be programmed to determine that the eye 235 has "fixated" for, say, one second before it produces a signal to CRT 226 commanding that the chosen symbol be fixed. Thus, the operator will first "fixate" on a chosen symbol in display 228 for, say, one third to one half of a second, will then move his gaze upward along face 225 while the chosen symbol is generated and moved to follow his eye movements, and then when the chosen symbol is properly placed, the operator will set the symbol in place by staring at the chosen position for one second. Thereafter, he may repeat the procedure with additional symbols from display 228 and thus produce a desired circuit diagram on the face 225 of CRT 226.

In the event that the operator wishes to remove or change a symbol already appearing on the face 225, an "erase" symbol, such as "E", in square 252 of display 228 may be employed. The operator, upon determining that a symbol previously set on face 225 should be removed, would first fixate on square 252, and would then set his gaze upon the portion of the circuit on face 225 to be removed for a predetermined period, say one second. Computer 240 would determine that eye 235 had fixated on square 252 and would then be programmed to detect a one second fixation which would follow. Upon determining the area on the face 225 where this fixation occurs, computer 240 would produce a signal to CRT 226 to erase the symbol chosen.

Other ways of setting or erasing a symbol on the face 225 of CRT 226 may also be employed. For example, computer 240 could be programmed to detect a blink or series of blinks to perform the desired operations.

Many other applications of the present invention will occur to those skilled in the art. For example, machine operators could have a display which would produce machine operations merely by the operator's eye movement and fixations. While the display 23 has been shown as produced by an optical projector 21, the projector is not necessary and the display can be a permanent display mounted in the operator's field of view.

I do not wish to be limited to the specific embodiments described here in connection with the preferred embodiment but rather intend to be limited only by the appended claims.

I claim:
1. In combination:
a surface to be observed, including a display area and a plurality of trigger areas adjacent thereto which represent different control functions desired to be performed;
means continuously giving an output representing the location of the point of intersection of an observer's line of sight with said surface;
means deriving, from said output, signals indicative that the observer has fixated for a predetermined time period on any of said trigger areas;
and means for performing one of the control functions in accordance with said signals.

2. Apparatus according to claim 1 in which said output comprises components representative of the abscissa and ordinate of said point on an arbitrary coordinate system coordinated with said surface.

3. Apparatus according to claim 1 in which the last named means comprises means for producing any of a plurality of displays on said display area, as determined by said signals.

4. Apparatus according to claim 1 in which the second named means comprises means sampling said output at predetermined intervals, continuously determining a running average of a predetermined latest number of said samples, and their deviations therefrom, and supplying an output signal when said deviations are all of less than a predetermined magnitude.

5. Apparatus according to claim 1 in which the second named means comprises means supplying an output when said point of intersection lies within the limits of any of said trigger areas.

6. Apparatus according to claim 1 in which the second named means comprises means sampling said output at predetermined intervals, continuously determining a running average of a predetermined latest number of said samples, and their deviations therefrom, and supplying an output signal when said deviations are all of less than a predetermined magnitude, together with means supplying an output when said point of intersection lies within the limits of any of said trigger areas.

7. Apparatus according to claim 1 in which the last named means comprises means for selecting an array of data determined by a first fixation, and for displaying said array at a location in said display area determined by a second fixation.

8. Apparatus for producing images on a viewing screen in accordance with the eye movements of an operator, comprising in combination:
a plurality of trigger areas on the viewing screen;
first means for producing a plurality of images on the viewing screen;
second means for determining the direction in which the eye of the operator is looking and producing a first signal indicative thereof;
third means connected to said second means to receive the first signal, said third means operable to analyze the first signal to detect which of the trigger areas the operator is looking at and determine the length of time the operator continues to look at such trigger area, said third means operable to produce a second signal only when the operator has looked at a trigger area for a predetermined time period, the second signal having a characteristic which depends on which of the trigger areas the operator is looking at; and
means connecting said third means to said first means so that the second signal causes said first means to produce a selected one of the plurality of images on the viewing screen in accordance with the characteristic of the second signal.

* * * * *